United States Patent [19]

Yamazaki et al.

[11] Patent Number: 4,940,662

[45] Date of Patent: Jul. 10, 1990

[54] LOW-MOLECULAR WEIGHT PEPTIDE MIXTURE AND METHOD OF PRODUCING SAME

[75] Inventors: Ken-ichi Yamazaki, Kawagoe; Shoji Takao, Higashikurume; Koji Yamamoto, Kawasaki, all of Japan

[73] Assignee: Terumo Kabushiki Kaisha, Tokyo, Japan

[21] Appl. No.: 794,322

[22] Filed: Nov. 1, 1985

Related U.S. Application Data

[63] Continuation of Ser. No. 471,793, Mar. 3, 1983, abandoned.

[30] Foreign Application Priority Data

Mar. 6, 1982 [JP] Japan .................................. 57-35485

[51] Int. Cl.$^5$ ...................... C12P 21/00; C12P 21/06; C12N 9/48; C07K 3/12
[52] U.S. Cl. ..................................... 435/68.1; 435/68; 435/212; 435/219; 435/272; 426/651; 426/656; 426/46; 426/49; 426/52; 426/18
[58] Field of Search .................... 435/68, 69, 212, 219, 435/272; 426/654, 656, 46, 49, 52, 18

[56] References Cited

U.S. PATENT DOCUMENTS

| | | | |
|---|---|---|---|
| 3,803,327 | 4/1974 | Fujimaki et al. | 426/32 |
| 3,904,519 | 9/1975 | McKinney et al. | 210/654 |
| 4,016,147 | 4/1977 | Fujimaki et al. | 260/112 R |
| 4,087,388 | 5/1978 | Jensen et al. | 521/61 |
| 4,145,455 | 3/1979 | Fujimaki et al. | 426/614 |
| 4,452,888 | 6/1984 | Yamazaki et al. | 435/69 |

FOREIGN PATENT DOCUMENTS

| | | | |
|---|---|---|---|
| 0889532 | 11/1981 | Belgium | 435/68 |
| 47879 | 3/1982 | European Pat. Off. | 435/68 |
| 2079758 | 1/1982 | United Kingdom | 435/68 |

OTHER PUBLICATIONS

Yamashita et al., *J. Agric. Food Chem.*, vol. 27(1), 1979, "A One-Step Process for Incorporation of L-Methionine into Soy Protein by Treatment with Papain".
Hanson, "Peptides 1972," (1973), pp. 355-362.
Chem. Abstracts, vol. 92, (1980), 126939f.
Chem. Abstracts, vol. 90, (1979), 70795v.
Chem. Abstracts, vol. 91, (1979), 54886r.

*Primary Examiner*—Robin L. Teskin
*Attorney, Agent, or Firm*—Frishauf, Holtz, Goodman & Woodward

[57] ABSTRACT

A method of producing a low-molecular weight peptide mixture, comprising the steps of dissolving a first protease in a buffer solution adjusted to an optimum pH for the protease ranging from pH 3 to 10, adding at least one first protein in a buffer solution having a pH of from 3 to 10 and a concentration of 10 to 60% by weight of the protein material and thoroughly mixing the solution, adding a solution of an ester of at least one amino acid pre-formed by esterification of the amino acid with an alcohol, the pH of said buffer solution being optimum for the incorporation of said amino acid in said starting protein in the presence of said first protease in a plastein reaction, reacting said ester of at least one amino acid with said starting protein in a plastein reaction in the mixed solution whereby said at least one amino acid is covalently incorporated into said starting protein to produce a plastein reaction solution containing a modified protein, hydrolyzing said modified protein using at least one second protease having a different specificity from said at least one first protease to produce a low-molecular weight peptide mixture having an amino acid content which has different proportions of amino acids than does said starting protein, and separating from the solution said low-molecular weight peptide mixture which comprises a major proportion of dipeptides and tripeptides and containing not more than 15% by weight of free amino acids and not more than 20% by weight of a high-molecular weight fraction of compounds having a molecular weight of not lower than 700 and removable by gel filtration. The said low-molecular weight peptide mixture is readily absorbable and a useful nutrient.

4 Claims, No Drawings

LOW-MOLECULAR WEIGHT PEPTIDE MIXTURE AND METHOD OF PRODUCING SAME

This application is a continuation of application Ser. No. 471,793, filed Mar. 3, 1983, now abandoned.

BACKGROUND OF THE INVENTION

1. Field of the Invention

This invention relates to a low-molecular weight peptide mixture mainly based on dipeptides and tripeptides and a method of producing such a low-molecular weight peptide mixture by incorporating one or more different amino acids covalently into protein by making use of the plastein reaction to thereby form a protein-like material having a modified amino acid composition, and hydrolyzing the protein-like material with a protease to produce a low-molecular with peptide mixture containing peptides having a residue of the amino acid or amino acids incorporated.

2. Description of Prior Art

Traditional nitrogen sources used for nutrition are protein materials, protein hydrolyzates, free amino acid mixtures and the like. It was recently found that low-molecular weight peptides such as di- and tri-peptides play a great role in enteral absorption as described in "Peptide Transport and Hydrolysis" (Elesevier Excepta Media North, Holland, 1977).

The inventors also found that a low-molecular weight peptide mixture mainly based on di- and tri-peptides is a dietetically improved nitrogen source (see Japanese Patent Application No. 55-94169). However, unlike a mixture of free amino acids, a low-molecular weight peptide mixture resulting from hydrolysis of protein material has the disadvantage that its amino acid composition is essentially dependent on that of the starting protein. When a protein material having a limiting amino acid is used or when the amino acid composition should be artificially tailored for the purpose of increasing the content of a particular amino acid, a possible solution is to add a free amino acid to make up the limiting or particular amino acid. Nevertheless, since peptides are enterally absorbed faster than free amino acids and encounter no antagonism upon absorption, it is desirable that such replenishing amino acids are added in the form of peptides.

Making extensive investigations on the production of a low-molecular weight peptide mixture in which the amino acids content of peptide is modified, the inventors have succeeded in producing a desired low-molecular weight peptide mixture by incorporating one or more different amino acids into a protein material through peptide linkages using the plastein reaction and hydrolyzing the resulting modified protein material with a protease.

Although proteolytic enzymes or proteases generally act to decompose peptide linkages, the reaction is rather reversed toward the synthesis of peptide linkages by increasing the substrate concentration. This reverse reaction is called plastein reaction. It is known that when the plastein reaction is used to cause amino acids to act on a protein material, there is obtained a modified protein material in which the amino acids are incorporated in the protein through peptide linkages. When amino acids are incorporated into protein by the reverse reaction of proteolysis, the concentration of protein in a substrate is set to a level from 10% to 60% by weight and higher than in normal hydrolytic reaction and the pH value for the plastein reaction is set more alkaline by pH 2-3 than the optimum pH for the same protease in normal hydrolytic reaction. By carrying out the plastein reaction under such conditions, a modified protein material having particular amino acids covalently incorporated through peptide linkages is produced.

However, it has never been attempted to incorporate at least one amino acid covalently into a protein material through peptide linkages by a simple process.

In incorporating an amino acid covalently into a protein material, the amino acid should be converted into an active form, for example, an ester prior to the reaction because the reaction does not proceed with a free amino acid. A number of methods are known for the esterification of amino acids, including hydrochloric acid, sulfuric acid, and thionyl chloride methods. Improvements are also made in the purification of the resulting amino acid ester. The ester prepared by any of these methods, however, is too expensive for commercial use as long as it must be isolated and purified before use. It is also undesirable in view of safety to the human body to use organic solvents or other chemicals for the purpose of isolating and purifying the amino acid ester. When safety and economy are taken into account, the process is desired to be as simple as possible and use no extra chemicals.

SUMMARY OF THE INVENTION

It is, therefore, an object of the present invention to produce a low-molecular weight peptide mixture by incorporating at least one desired amino acid covalently into a starting protein by a simple process to thereby form a modified protein material, and subjecting the modified protein material to hydrolysis with a protease to produce a low-molecular weight peptide mixture containing peptides having the amino acid in the form of an amino acid residue.

The above object is attained by a method for producing a low-molecular weight peptide mixture according to the present invention, which comprises the steps of dissolving a first protease in a buffer solution adjusted to an optimum pH for the protease ranging from pH 3 to 10, adding a starting protein material to the buffer solution to a concentration of 10 to 60% by weight of the protein material and thoroughly mixing the solution, adding a solution of an ester of at least one amino acid pre-formed by esterification of the amino acid with an alcohol, causing plastein reaction to take place in the mixed solution, thereby incorporating said at least one amino acid into said starting protein material by peptide linkages to produce a modified protein material, subjecting the modified protein material to hydrolysis using a second protease having a different specificity from the first protease used in said plastein reaction, and separating from the solution a low-molecular weight peptide mixture mainly based on dipeptides and tripeptides and containing not more than 15% by weight of free amino acids and not more than 20% by weight of a high-molecular weight fraction of compounds having a molecular weight of not lower than 700 and removable by gel filtration.

In a preferred embodiment of the invention, at least one first protease selected from the group consisting of papain, bromelain, and ficin is used in the enzymatic or plastein reaction for incorporating at least one amino acid into the starting protein material. In effecting hydrolysis of the protein-like material or modified protein having at least one amino acid incorporated, preferably two or more second proteases selected from the group consisting of pepsin, molsin, and orientase are simultaneously or successively added to an aqueous solution prepared so as to contain 3 to 20% by weight of the modified protein material and the proteolytic or hydrolytic reaction is carried out at a temperature of 25°–60° C. for 8 to 72 hours. Preferably, the reaction solution of the modified protein material in which at least one amino acid is incorporated covalently into the original protein material may be purified by repeated concentration operations using a reverse osmosis membrane having NaCl rejection of not higher than 40%, preferably 5 to 20%, thereby removing inorganic salts and unreacted amino acid, amino acid ester and other low-molecular weight impurities from the reaction solution, before the reaction solution is subjected to the subsequent hydrolysis. Ethyl alcohol is the best alcohol for use in esterifying the amino acid to be incorporated into the starting protein material.

The inventors have found that a modified protein having the desired amino acids incorporated covalently can be produced by selecting an alcohol, preferably ethyl alcohol for the esterification of the amino acids in view of safety to the human body, and simultaneously adding reaction solutions of at least two different amino acid esters to a starting material without isolating or purifying the amino acids esters, and effecting a plastein reaction to incorporate the amino acids (see Table 4). The esterification of amino acids to be incorporated into the protein may preferably be carried out in the presence of a catalyst which should be a mineral acid such as hydrochloric acid and sulfuric acid or an organic acid such as phosphoric acid in consideration of the fact that the final product is administered to the human body. When such an acid catalyst is used, neutralization of the reaction solution which has completed the amino acid-incorporating reaction forms a substantial amount of salt. The content of salt in a product obtained after the amino acid-incorporating reaction may be reduced by using concentrated sulfuric acid as the esterification catalyst, adding sodium carbonate to the reaction solution of the amino acid ester, and removing the resulting precipitate of sodium sulfate from the reaction solution prior to the amino acid-incorporating reaction, or alternatively by using an organic acid capable of forming an insoluble calcium salt, such as phosphoric acid as the esterification catalyst, adding calcium carbonate to an esterification solution, removing the resulting insoluble calcium salt such as calcium phosphate from the reaction solution prior to the amino acid-incorporating reaction. Since the esterification reaction solution is not completely free of salt after such salt removal and a buffer solution used in the amino acid-incorporating reaction will add to the salt in the reaction solution, preferably the unreacted amino acids, amino acid esters and low-molecular weight impurities are subsequently removed from the reaction solution. A study on the desalting and purification of such a reaction solution has revealed that favorable results are available by repeatedly concentrating the reaction solution of a modified protein material having amino acids incorporated using a reverse osmosis membrane having NaCl rejection of not higher than 40%, preferably 5–20%. Differently stated, the use of a reverse osmosis membrane having NaCl rejection lower than a certain level allows only inorganic salts and low-molecular weight impurities to be removed from the reaction solution while preventing the products from permeating through the membrane.

The reaction solution of at least one amino acid ester obtained at the end of esterification reaction is combined with a starting protein material to incorporate the amino acid covalently into the protein material by the following procedure. The starting material is prepared into a solution with a concentration of 10 to 60% by weight of protein before the reaction solution of amino acid ester is added to the protein material, and a protease or proteolytic enzyme is further added thereto. The resulting solution is adjusted to a pH value between 3 and 10 and more alkaline by pH 2 or 3 than the optimum pH for the protease used, for example, to pH 8 to 9 when papain is used. The enzymatic or plastein reaction is then carried out for 8 to 48 hours. The reaction temperature is controlled to the optimum temperature for the protease used. A protein-like material or modified protein is produced at the end of the enzymatic reaction in which the amino acid is incorporated covalently. According to the invention, the modified protein is further subjected to hydrolysis with another protease or proteolytic enzyme to produce a low-molecular weight peptide mixture containing peptides having the desired amino acid in the form of an acid residue. The content of free amino acids in the composition is desirably reduced to 15% by weight or lower in order to nutritional-physiologically take advantage of the increased absorption rate of peptides or to give rise to no substantial antagonism upon absorption of amino acids. In addition, the content of those peptides having a relatively higher molecular weight of 700 or more is desirably reduced to 20% by weight or lower so that initial absorption rate may not be reduced. In producing a low-molecular weight peptide mixture of a modified amino acid composition which is mainly based on di- and tri-peptides and contains not more than 15% by weight of free amino acids and not more than 20% by weight of peptides having a molecular weight of not lower than 700, the following feature is critical.

It is critical what combination of proteases or enzymes is used, one for the first reaction of incorporating a desired amino acid into a protein material and the other for the second reaction of hydrolyzing the modified protein material into a low-molecular weight peptide mixture so as to achieve the purpose of the invention. If an identical protease is used in both the reactions, the amino acid incorporated during the first or incorporation reaction would probably be liberated again during the second or hydrolytic reaction. If a protease preparation containing an active ingredient like carboxylpeptidase capable of liberating an amino acid from the end of a carboxyl group on polypeptides is used in the hydrolytic reaction, it would also cause the once incorporated amino acid to be liberated again. To prevent the amino acid from being liberated again in the course of hydrolysis, it is necessary to select proteases of different types, that is, proteases having significantly different specificity, such that the probability that the proteases used in the incorporation and hydrolytic reactions will act on the peptide linkages in the same positions is minimized, and to use in the hydrolytic reaction a protease having little peptidase activity.

Proteases or proteolytic enzymes are generally classified into the following four types in terms of structure and function.

(1) Serine protease trypsin, chymotrypsin, subtilin, nagase, etc.

(2) Thiol protease papain, bromelain, ficin, etc.

(3) Metal protease carboxy peptidase-A, etc.

(4) Acidic protease pepsin, molsin, orientase, etc.

Among these proteases, most proteases classified in the same type tend to beat least partially common or similar in specificity though not always. With respect to the combination of proteases used in the incorporation and hydrolytic reactions, it is advantageous to select them from different types for the purpose of preventing the amino acid once incorporated from being liberated again.

When a single protease which has high rates of incorporation and liberation, but has a substantial difference between these rates (as will be demonstrated in Reference Example and Table 4) is used in both the incorporation and hydrolytic reactions, the amount of an amino acid incorporated will be increased, but the amino acid which has been incorporated during the incorporation reaction will be liberated again during the hydrolytic reaction to increase the content of free amino acids, failing to obtain the desired low-molecular weight peptide mixture mainly based on di- and tri-peptides (see Example 6). In order to hydrolyze an amino acid-incorporated protein material with a protease into a mixture of di- and tri-peptides, a particular combination of proteases selected from different types should be used.

In the hydrolysis of a protein-like material or modified protein having one or more amino acids incorporated, the addition of two or three acidic proteases selected from pepsin, molsin, and orientase in a simultaneous or successive manner results in a low-molecular weight peptide mixture of a modified amino acid composition which is mainly based on di- and tri-peptides, and has a low content of free amino acids and a low proportion of a high-molecular weight fraction with a molecular weight of 700 or higher see Examples 1–5).

Such low-molecular weight peptide mixtures mainly based on di- and tri-peptides are excellent as a nitrogen source for nutrition because they are enterally absorbed rapidly and give rise to no antagonism upon absorption as free amino acids do, so that they are absorbed with little change in amino acid composition from the nitrogen source as administered.

With the recent advance in parenteral nutrition, enteral nutrition or the like, an attempt has been made to apply nutritional control to medical treatment. Particularly researches have been made from various aspects on the effect of so-called amino acid imbalance, that is, the effect of nutritional specificity resulting from the lack or excess of a particular amino acid in a nitrogen source to be administered to the patient. For example, it is known that in hepatic diseases such as hepatic encephalopathy and liver failure, the contents of amino acids such as phenylalanine, tyrosine and methionine in the plasma is increased while the contents of branched chain amino acids such as leucine, isoleucine and valine are decreased. It has been attempted as a treatment for such hepatic diseases to administer a nitrogen source having an increased content of branced chain amino acids. Also, an attempt has been made to apply arginine imbalance for the control of growth of a tumor. In preparing a nitrogen source destined for amino acid imbalance, the method for producing a low-molecular weight peptide mixture from a modified protein material having an amino acid incorporated according to the present invention will be advantageously used.

The invention will be more fully understood by reading the following examples which are given by way of illustration and should not be construed as limiting the scope of the invention. Unless otherwise stated, percents are by weight.

EXAMPLE 1

In 2.5 liters of water containing 85 g of sodium carbonate and 26 g of sodium hydrogen carbonate, were dissolved 33 g of papain and 3.3 g of L cysteine as a papain activator. With stirring, 1 kg of a commercial soybean protein (manufactured and sold by Fuji Seiyu K.K. under trade name "Fujipro R") in limited amounts was added to the solution and thoroughly mixed and agitated. Separately, a suspension of 50 g of L-methionine in 320 ml of ethyl alcohol was gradually added to 35 ml of conc. sulfuric acid to completely dissolve the methionine. The solution was heated under reflux at 90° C. for 5 hours, obtaining a reaction solution of L-methionine ethyl ester in an yield of 92.3%. The reaction solution was diluted with ethyl alcohol to a volume of 500 ml. A 370-ml portion of the diluted reaction solution was added to the separately prepared protein system. After thorough mixing and agitation, the solution was kept at 37° C. for 24 hours to effect plastein reaction. The yield of L methionine incorporated in the thus produced protein-like material was 88.1% based on the amount of L-methionine ethyl ester added at the start of the reaction. The reaction solution was then diluted with water to a volume of 20 liters and adjusted to pH 6–7 with hydrochloric acid before it was subjected to repeated concentration operations for desalting and purification using a reverse osmosis membrane (tubular type, manufactured by Daicell Chemical K.K. under tradename DRS-10) under an operating pressure of 15 kg/cm$^2$. The concentrate resulting from the reverse osmosis treatment was again diluted with water to a volume of 20 liters and adjusted to pH 3 with phosphoric acid. Then, 20 g of orientase (manufactured by Hankyu Kyoei Bussan K.K.) and 20 g of molsin (manufactured by Fujisawa Chemicals K.K.) were added to the solution, which was kept at 40° C. for 40 hours to effect hydrolysis. During the reaction, the solution was controlled to pH 3 with a 6N phosphoric acid. At the end of the reaction, the solution was heated to 90° C. for 10 minutes to deactivate the proteases. The solids were removed by filtration, and the filtrate was spray dried to yield 685 g of a dry powder, which was a low-molecular weight peptide mixture having L-methionine replenished in the form of an acid residue. The low-molecular weight peptide mixture was found to have an average molecular weight of 320. A sample of the powder was subjected to gel filtration using Cephadex G-10 to find that 87.3% of the sample had a molecular weight of 700 or lower. It was also found that the content of free amino acids was 9.8%. Table 1 shows the amino acid composition of the starting soybean protein and low-molecular weight peptide mixture produced therefrom.

TABLE 1

| Amino acid | (unit: % by weight) | |
|---|---|---|
| | Soybean protein | Product |
| Aspartic acid | 11.3 | 11.3 |
| Threonine | 3.8 | 3.3 |
| Serine | 4.9 | 4.6 |
| Glutamic acid | 19.3 | 20.4 |
| Proline | 5.6 | 5.7 |
| Glycine | 4.1 | 3.9 |
| Alanine | 4.2 | 3.5 |
| Cystine | 1.0 | 0.9 |
| Valine | 4.8 | 4.3 |
| Methionine | 1.3 | 4.2 |
| Isoleucine | 4.8 | 4.6 |
| Leucine | 7.8 | 6.9 |
| Tyrosine | 3.7 | 3.4 |
| Phenylalanine | 5.4 | 4.7 |
| Lysine | 6.3 | 6.5 |
| Histidine | 2.7 | 2.8 |
| Arginine | 7.9 | 7.8 |
| Tryptophane | 1.3 | 1.2 |

TABLE 2

| Amino acid | (unit: % by weight) | |
|---|---|---|
| | Wheat gluten | Product |
| Aspartic acid | 4.4 | 4.1 |
| Threonine | 2.8 | 2.6 |
| Serine | 4.8 | 4.5 |
| Glutamic acid | 31.9 | 29.5 |
| Proline | 12.1 | 10.9 |
| Glyine | 3.5 | 3.1 |
| Alanine | 2.4 | 2.0 |
| Cystine | 3.6 | 3.2 |
| Valine | 4.6 | 4.2 |
| Methionine | 1.7 | 4.3 |
| Isoleucine | 4.1 | 3.9 |
| Leucine | 7.2 | 6.8 |
| Tyrosine | 3.1 | 3.0 |
| Phenylalanine | 4.7 | 4.3 |
| Lysine | 2.3 | 7.2 |
| Histidine | 1.8 | 1.8 |
| Arginine | 3.9 | 3.6 |
| Tryptophane | 1.1 | 1.0 |

EXAMPLE 2

A solution of 2.2 g of L-lysine in 13.0 ml of ethyl alcohol and 1.6 ml of conc. sulfuric acid was heated under reflux at 90° C. for 5 hours, obtaining L-lysine ethyl ester in a yield of 76.5%. Separately, L-methionine ethyl ester was prepared from 0.8 g of L-methionine in the same manner as in Example 1. After 66 mg of papain and 6.6 mg of L-cysteine were dissolved in a solution of 1.8 g of sodium carbonate and 0.52 g of sodium hydrogen carbonate in 20 ml of water, 20 g of wheat gluten in limited amounts was added to the solution and mixed therewith. The previously prepared reaction solutions of L-lysine and L-methionine ethyl esters were all added to the protein system of wheat gluten, and the system was kept at 37° C. for 24 hours to effect plastein reaction. The rates of incorporation of L-lysine and L-methionine were 62.7% and 81.6%, respectively. At the end of the reaction, the reaction solution was diluted with water to a volume of 300 ml and adjusted to pH 7 with hydrochloric acid before it was subjected to repeated concentration operations for desalting and purification using a reverse osmosis membrane equipped small experimental apparatus (equipped with a DRS-10 flat membrane, manufactured by Daicell Chemical K.K.) under an operating pressure of 15 kg/cm². The concentrate resulting from the reverse osmosis treatment was again diluted with water to a volume of 400 ml and adjusted to pH 2.0 with phosphoric acid. After 0.4 g of pepsin was added to the solution, the hydrolytic reaction was carried out for 3 hours. Thereafter, 0.4 g of orientase was added and the hydrolytic reaction was continued for an additional 30 hours. The reaction solution was heated to 90° C. for 10 minutes and then centrifuged under 2000G to remove the solids. The supernatant was freeze dried to yield 18.3 g of a low-molecular weight peptide mixture. This product had an average molecular weight of 350 and contained 8.9% of free amino acids, and the gel filtration showed that it contained 86.2% of compounds with a molecular weight of 700 or lower. Table 2 shows the amino acid composition of the starting protein, wheat gluten and the low-molecular weight peptide mixture produced therefrom. As seen from Table 2, the low-molecular weight peptide mixture had the increased contents of L-lysine and L-methionine as compared with the starting protein.

EXAMPLE 3

110 g of L-valine, 140 g of L-isoleucine, and 70 g of L-leucine were suspended in 700 ml, 800 ml, and 440 ml of ethyl alcohol and dissolved in 80 ml, 100 ml, and 50 ml of conc. sulfuric acid, respectively. These solutions were individually heated under reflux at 90° C. for 5 hours to effect esterification. The degrees of esterification were 78.6% for L-valine, 67.7% for L-isoleucine, and 90.3% for L-leucine. Separately, 33 g of papain and 3.3 g of L-cysteine were dissolved in a solution of 85 g of sodium carbonate and 26 g of sodium hydrogen carbonate in 3 liters of water. With stirring, 1 kg of a commercial soybean protein ("Fujipro R") in limited amounts was added to the solution and thoroughly mixed therewith. The previously prepared reaction solutions of amino acid esters were added to this protein system. In this example, the ethanol in each reaction solution of amino acid ester was previously distilled off to a one-half volume in consideration of the influence of the alcohol on protease activity. The solution was kept at 37° C. for 30 hours to effect plastein reaction. The thus produced protein-like material had L-valine, L-isoleucine and L-leucine incorporated in an yield of 63.5%, 69.2% and 91.4% based on the ethyl esters used, respectively. The resulting reaction solution was diluted with water to a volume of 50 liters and adjusted to pH 6–7 with hydrochloric acid before it was subjected to repeated concentration operations for desalting and purification using a reverse osmosis membrane (tubular type, manufactured by Daicell Chemical K.K. under tradename "DRS-40") under an operating pressure of 30 kg/cm². The concentrate resulting from the reverse osmosis treatment was again diluted with water to a volume of 20 liters and adjusted to pH 3 with phosphoric acid, and 20 g of orientase and 20 g of molsin were added to the solution. The solution was kept at 40° C. for 48 hours to effect hydrolysis while it was controlled to pH 3 with a 6N phosphoric acid. The reaction solution was heated to 90° C. for 10 minutes to deactivate the proteases, neutralized, and then filtered to remove the solids. The filtrate was spray dried to yield 703 g of a dry powder. The thus obtained low molecular weight peptide mixture having an increased content of branched chain amino acids had an average molecular weight of 300. This mixture contained 89.6% of compounds with a molecular weight of 700 or less and 12.1% of free amino acids. Table 3 shows the amino acid composition of the starting soybean protein and the low-molecular weight peptide mixture produced therefrom. As seen from Table 3, the mixture produced had increased contents of the branched chain amino acids, L valine, L-isoleucine and L-leucine as compared with the starting soybean protein.

TABLE 3

| Amino acid | (unit: % by weight) | |
|---|---|---|
| | Soybean protein | Product |
| Aspartic acid | 11.3 | 9.6 |
| Threonine | 3.8 | 3.2 |
| Serine | 4.9 | 4.2 |
| Glutamic acid | 19.3 | 16.4 |
| Proline | 5.6 | 4.8 |
| Glycine | 4.1 | 3.5 |
| Alanine | 4.2 | 3.6 |
| Cystine | 1.0 | 0.9 |
| Valine | 4.8 | 8.7 |
| Methionine | 1.3 | 1.1 |
| Isoleucine | 4.8 | 9.4 |
| Leucine | 7.8 | 11.4 |
| Tyrosine | 3.7 | 3.2 |
| Phenylalanine | 5.4 | 4.6 |
| Lysine | 6.3 | 5.4 |
| Histidine | 2.7 | 2.3 |
| Arginine | 7.9 | 6.7 |
| Tryptophane | 1.3 | 1.1 |

EXAMPLE 4

A low-molecular weight peptide mixture was produced from a protein-like material in which L-methionine was introduced into soybean protein by repeating the procedure of Example 1 except that papain was replaced by bromelain in the early stage of incorporating L-methionine, and orientase and molsin were replaced by 20 g of pepsin and 20 g of molsin in the late stage of hydrolysis. The rate of incorporation of L-methionine ethyl ester was 79.4%. The low-molecular weight peptide mixture had an average molecular weight of 350, and contained 7.9% of free amino acids and 83.6% of a fraction with a molecular weight of 700 or lower.

Similar results were obtained when the bromelain was replaced by ficin in this example.

EXAMPLE 5

A low-molecular weight peptide mixture was produced from a protein-like material in which L-valine, L-isoleucine and L-leucine were incorporated into soybean protein, by repeating the procedure of Example 3 except that three proteases, 20 g of pepsin, 20 g of orientase and 20 g of molsin were used instead of the orientase and molsin in the late stage of hydrolysis. The low molecular weight peptide mixture had substantially the same amino acid composition as in Example 3, but had an average molecular weight of 290 and contained 90.2% of a fraction with a molecular weight of 700 or lower and 12.3% of free amino acids.

COMPARATIVE EXAMPLE

A low-molecular weight peptide mixture was produced from a protein-like material in which L-methionine was incorporated into soybean protein using papain, by repeating the procedure of Example 1 except that 40 g of pepain was used instead of the orientase and molsin in the late stage of hydrolysis. As a result, the amount of free methionine in the product was 37.9% based on the amount of L-methionine added to the starting protein and the total content of free amino acids was 41.2%.

REFERENCE EXAMPLE

L-methionine was incorporated into 500 g of soybean protein in the same manner as in Example 1 and the resulting protein-like material was hydrolyzed into a low-molecular weight peptide mixture. In this example, various combinations of proteases were used in both the early stage of incorporating the amino acid and the late stage of hydrolyzing the protein-like material. Table 4 shows, for various proteases, the rate of incorporation of L-methionine and the rate of liberation of L-methionine (percentage of L-methionine liberated again in the late stage of hydrolysis relative to the L-methionine once incorporated).

TABLE 4

| Incorporation reaction | | | Hydrolytic reaction | | |
|---|---|---|---|---|---|
| Protease | pH | Incorporation rate (%) | Protease | pH | Liberation rate (%) |
| Papain | 9 | 88.3 | Papain | 7 | 37.9 |
| Papain | 9 | 88.3 | Bromelain | 7 | 32.2 |
| Papain | 9 | 88.3 | Molsin | 3 | 7.8 |
| Papain | 9 | 88.3 | Pepsin | 2 | 2.1 |
| Bromelain | 9 | 76.4 | Bromelain | 7 | 35.7 |
| Bromelain | 9 | 76.4 | Papain | 7 | 33.9 |
| Bromelain | 9 | 76.4 | Molsin | 3 | 7.3 |
| Pepsin | 4 | 58.9 | Pepsin | 2 | 3.6 |
| Pepsin | 4 | 58.9 | Papain | 7 | 28.4 |
| Pepsin | 4 | 58.9 | Molsin | 3 | 7.6 |
| Trypsin | 9 | 12.1 | Trypsin | 7 | 49.7 |
| Trypsin | 9 | 12.1 | Pepsin | 2 | 1.8 |
| Chymotrypsin | 9 | 45.6 | Chymotrypsin | 7 | 41.5 |
| Chymotrypsin | 9 | 45.6 | Molsin | 3 | 7.5 |
| Subtilin | 9 | 41.8 | Subtilin | 7 | 36.2 |
| Subtilin | 9 | 41.8 | Molsin | 3 | 7.4 |
| Molsin | 5 | 28.5 | Molsin | 3 | 10.1 |
| Molsin | 5 | 28.5 | Orientase | 3 | 8.0 |
| Molsin | 5 | 28.5 | Papain | 7 | 31.7 |
| Orientase | 5 | 21.7 | Orientase | 3 | 12.4 |
| Orientase | 5 | 21.7 | Bromelain | 7 | 29.7 |
| Nagase | 9 | 48.1 | Nagase | 7 | 37.1 |
| Nagase | 9 | 48.1 | Pepsin | 2 | 1.9 |
| Pronase | 9 | 17.4 | Pronase | 7 | 52.6 |
| Pronase | 9 | 17.4 | Pepsin | 3 | 2.3 |

The present invention has the following advantages.

(1) According to the present invention, a limiting or desired amino acid is incorporated into a starting protein material and a low-molecular weight peptide mixture mainly based on di- and tri-peptides is produced from such a protein-like material or modified protein while minimizing the formation of free amino acids and relatively high molecular weight peptides. The present invention thus provides a method for producing a peptide mixture whose amino acid composition has never been contemplated i.e., is unique. This unique peptide mixture is free of any problem associated with antagonism upon absorption of amino acids, that is, improved in amino acid absorption, and thus free of the drawbacks of conventional high-molecular weight peptide mixtures which have low absorption efficiency because of their high molecular weight of several thousand or more, or peptide mixtures whose amino acid composition is dependent on a starting protein material.

(2) When a limiting or desired amino acid is incorporated into a starting protein material and a low-molecular weight peptide mixture mainly based on di- and tri-peptides is produced from such a protein-like material or modified protein while minimizing the formation of free amino acids and relatively high molecular weight peptides, the protease used to incorporate the amino acid into the starting protein and the protease used to hydrolyze the protein-like material into low-molecular weight peptides should be of a specific combination as described above. This specific combination of proteases permits a useful low-molecular weight peptide mixture to be produced in relatively pure form by a simple process.

(3) The method of the present invention does not use a reaction system which might be harmful to the human body and purifies the intermediate product by removing impurities such that the final product may be used safely without further purification. The peptide mixture of the present invention is readily absorbed enterally and gives rise to no antagonism phenomenon as co-existing amino acids do, so that it provides a nutritional-physiologically improved nitrogen source.

(4) The method of the present invention provides a low-molecular weight peptide mixture in which a limiting amino acid of a starting protein material or desired amino acid which is regarded necessary for medical treatment or physiological purpose is incorporated into the protein material in readily absorbable form. Such a peptide mixture may find great use as nutritious and treating agents.

What we claim is:

1. A method of producing a low-molecular weight peptide mixture comprising a major proportion of dipeptides and tripeptides produced from a starting natural protein to which at least two desired amino acids are incorporated, said at least two desired amino acids being the ones whose contents in the starting protein are low, whereby said dipeptides and tripeptides have a modified amino acid composition different from an amino acid composition of said starting protein, comprising the steps of dissolving at least one alkaline protease selected from the group consisting of papain, bromelain and ficin, in a buffer solution adjusted to an optimum pH for the protease up to 10, adding at least one starting protein in a buffer solution having an alkaline pH up to 10 and a concentration of 10 to 60% by weight of the protein material and thoroughly mixing the solution, adding at least two ethyl esters of amino acids, said amino acids being selected from the group consisting of L-lysine, L-methionine, L-valine, L-isoleucine and L-leucine, the pH of said buffer solution being optimum for the incorporation of said amino acid in said starting protein in the presence of said alkaline protease in a plastein reaction, reacting said ester of at least two amino acids with said starting protein in a plastein reaction in the mixed solution having an alkaline pH whereby said at least two amino acids are covalently incorporated into said starting protein to produce a plastein reaction solution containing a modified protein, subjecting said plastein reaction solution to concentration using a reverse osmosis membrane having an NaCl rejection of not higher than 40% to thereby purify said reaction solution by removing inorganic salts, unreacted amino acid and amino acid ester, and other low-molecular weight impurities from the reaction solution, and forming an aqueous solution containing 3 to 20% by weight of said modified protein, hydrolyzing said modified protein in said purified aqueous solution by simultaneously or successively adding at least two acidic proteases having different specificity than said at least one alkaline protease, said acidic proteases being selected from the group consisting of pepsin, molsin and orientase, to said aqueous solution containing 3 to 20% by weight of said modified protein at an acidic pH, and maintaining a reaction temperature of 25° to 60° C. for from 8 to 72 hours to produce a low-molecular weight peptide mixture having an amino acid content which has different proportions of amino acids than does said starting protein, and separating from the hydrolyzed solution said low-molecular weight peptide mixture which comprises a major proportion of dipeptide and tripeptides and containing not more than 15% by weight of free amino acids and not more than 20% by weight of a high-molecular weight fraction of compounds having a molecular weight of not lower than 700 and removable by gel filtration.

2. The method of producing a low-molecular weight peptide mixture of claim 1 wherein said plastein reaction is carried out at a pH which is higher than the inherent optimum pH of said at least one alkaline protease by a pH of 2 to 3.

3. The method of producing a low-molecular weight peptide mixture according to claim 1 wherein said at least two ethyl esters of amino acids are L-lysine ethyl ester and L-methionine ethyl ester.

4. The method of producing a low-molecular weight peptide mixture according to claim 1 wherein said at least two ethyl esters of amino acids are L-valine ethyl ester, L-isoleucine ethyl ester and L-leucine ethyl ester.

* * * * *

UNITED STATES PATENT AND TRADEMARK OFFICE
CERTIFICATE OF CORRECTION

PATENT NO. : 4,940,662
DATED : July 10, 1990
INVENTOR(S) : YAMAZAKI et al It is certified that error appears in the above-identified patent and that said Letters Patent is hereby corrected as shown below:

Title page, Section [56] References Cited, insert under "FOREIGN PATENT DOCUMENTS":

--2,909,854  10/1979  Germany--.

Column 1, line 18,:

Change "with" to --weight--.

Signed and Sealed this

Third Day of November, 1992

Attest:

DOUGLAS B. COMER

*Attesting Officer*     *Acting Commissioner of Patents and Trademarks*